United States Patent
Müller et al.

(10) Patent No.: US 6,624,318 B1
(45) Date of Patent: Sep. 23, 2003

(54) PROCESS FOR THE EPOXIDATION OF AN ORGANIC COMPOUND WITH OXYGEN OR AN OXYGEN-DELIVERING COMPOUNDS USING CATALYSTS CONTAINING METAL-ORGANIC FRAME-WORK MATERIALS

(75) Inventors: Ulrich Müller, Neustadt (DE); Lisa Lobree, Mannheim (DE); Michael Hesse, Worms (DE); Omar M. Yaghi, Ann Arbor, MI (US); Mohamed Eddaoudi, Ann Arbor, MI (US)

(73) Assignees: BASF Aktiengesellschaft, Ludwigshafen (DE); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 10/157,494

(22) Filed: May 30, 2002

(51) Int. Cl.[7] ................... C07D 301/04; C07D 301/12; C07D 301/19
(52) U.S. Cl. ................. 549/529; 549/523; 549/531; 549/533; 549/534; 549/536
(58) Field of Search ................ 549/529, 523, 549/531, 533, 534, 536

(56) References Cited

U.S. PATENT DOCUMENTS 5,648,508 A   7/1997   Yaghi ................... 556/9

FOREIGN PATENT DOCUMENTS

EP   0 709 253   8/1997

OTHER PUBLICATIONS

M. O'Keeffe, et al., Frameworks for Extended Solids: Geometrical Design Principles, Journal of Solid State Chemistry, 152, pp. 3–20, 2000.

Haillian Li, et al., Design and synthesis of an exceptionally stable and highly porous metal–organic framework, Letters to Nature, Nature, vol., 402, pp. 276–279, Nov. 1999.

Banglin Chen, et al., Interwoven Metal–Organic Framework on a Periodic Minimal Surface with Extra–Large Pores, Science, vol. 291, pp. 1021–1023, Feb. 9, 2001.

*Primary Examiner*—Ba K. Trinh
(74) *Attorney, Agent, or Firm*—Oblon, Spivak, McClelland, Maier & Neustadt, P.C.

(57) ABSTRACT

The present invention relates to a process for the reaction of at least one organic compound with one oxygen-delivering substance, for example a hydroperoxide, in the presence of at least one catalyst containing a metal-organic framework material comprising pores and a metal ion and an at least bidentate organic compound, said bidentate organic compound being coordinately bound to the metal ion. Further, the present invention is directed to the products being obtainable by the process according to the invention.

18 Claims, No Drawings

US 6,624,318 B1

PROCESS FOR THE EPOXIDATION OF AN ORGANIC COMPOUND WITH OXYGEN OR AN OXYGEN-DELIVERING COMPOUNDS USING CATALYSTS CONTAINING METAL-ORGANIC FRAME-WORK MATERIALS

The present invention relates to a process for the epoxidation of at least one organic compound with oxygen or an oxygen-delivering compound, in the presence of at least one catalyst containing a metal-organic framework material comprising pores and a metal ion and an at least bidentate organic compound, said bidentate organic compound being coordinately bound to the metal ion. Further, the present invention is directed to the products being obtainable by the process according to the invention.

Reactions of organic compounds with oxidizing agents as hydroperoxides are well known in the prior art, for example from DE 100 55 652.3 and further patent applications of the present applicant, such as DE 100 32 885.7, DE 100 32 884.9 or DE 100 15 246.5.

The state of the art for catalysts used in epoxidation reactions is given by materials containing zeolites, in particular catalysts which comprise a titanium-, vanadium-, chromium-, niobium- or zirconium-containing zeolite as a porous oxidic material. Such catalysts are described, for example, in WO 00/07965.

In a promising novel and alternative strategy to create micro- and/or mesoporous catalytically active materials, metal ions and molecular organic building blocks are used to form so-called metal-organic frameworks (MOFs). The metal-organic framework materials as such are described, for example, in. U.S. Pat. No. 5,648,508, EP-A-0 709 253, M. O'Keeffe et al., *J. Sol. State Chem.*, 152 (2000) p. 3–20, H. Li et al., *Nature* 402 (1999) p. 276 seq., M. Eddaoudi et al., *Topics in Catalysis* 9 (1999) p. 105–111,B. Chen et al., *Science* 291 (2001) p. 1021–23. Among the advantages of these novel materials, in particular for applications in catalysis, are the following:

(i) larger pore sizes can be realized than for the zeolites used presently
(ii) the internal surface area is larger than for porous materials used presently
(iii) pore size and/or channel structure can be tailored over a large range
(iv) the organic framework components forming the internal surface can be functionalized easily.

However, these novel porous materials have only been described as such. The use of these catalytically active materials in reactions of technical importance, in particular for epoxidation reactions, has not been disclosed yet.

It is an object of the present invention to provide a catalyst for the reaction of organic compounds with oxygen and/or oxygen-delivering compounds, wherein the catalyst for said reaction contains a novel material, in addition to, or instead of, catalytic materials according to the prior art, particularly in addition to, or instead of, zeolites.

This object is solved by providing a process for the epoxidation of at least one organic compound with oxygen and/or at least one oxygen-delivering compound in the presence of a catalyst, wherein said catalyst contains a metal-organic framework material comprising pores and at least one metal ion and at least one at least bidentate organic compound, which is coordinately bound to said metal ion.

As epoxidation agents, oxygen and oxygen-delivering compounds can be used. This includes but is not limited to ozone, water, oxidizing enzymes, reactive oxides, such as permanganates, chromic oxide, nitric oxide and the like. If oxygen is used, the gas may be mixed with other reactive gases and/or inert gases. Preferred are hydroperoxides known from the prior art which are suitable for the reaction of the organic compound. Mixtures of at least two of the aforementioned epoxidation agents are included as well. The generic formula of a hydroperoxide can be given as R—O—O—H. In principle, any organic or inorganic entity known to the expert in the field may be used as the group "R". Examples of such hydroperoxides are tertbutyl hydroperoxide, ethylbenzene hydroperoxide, and cumene-hydroperoxide. In the present invention, preference is given to using hydrogen peroxide as hydrol peroxide. The present invention therefore also provides a process as described above, in which the hydroperoxide used is hydrogen peroxide. Preference is given to using an aqueous hydrogen peroxide solution. The hydrogen peroxide, or any hydroperoxide for that matter, can be either prepared outside the reaction or by starting from hydrogen and oxygen, or other suitable components, in situ within the reaction.

With respect to epoxidation reactions, DE 100 55 652.3, DE 100 32 885.7, DE 100 32 884.9, DE 100 15 246.5, DE 199 36 547.4, DE 199 26 725.1, DE 198 47 629.9, DE 198 35 907.1, DE 197 23 950.1 are fully encompassed within the content of the present application with respect to their respective content.

Other known processes for epoxidation reactions are not excluded from the present application, and are, for example, described in Weissermel, Arpe "Industrielle Organische Chemie", publisher VCH, Weinheim, 4$^{th}$ Ed., pages 288 to 318 and in U. Onken, Anton Behr, "Chemische Prozesskunde", Vol. 3, Thieme, 1996, pages 303 to 305 as well as Weissernel, Arpe "Industrial Organic Chemistry", 5$^{th}$ Ed., Wiley, 1998, pages 159 to 181.

Among the reactions which are possible in the process of the present invention, the following are mentioned by way of example and without limiting the general scope of the present invention:

the epoxidation of olefins, e.g. the preparation of propylene oxide from propylene and $H_2O_2$ or from propylene and mixtures which provide $H_2O_2$ in situ;

hydroxylations such as the hydroxylation of monocyclic, bicyclic or polycyclic aromatics to give monosubstituted, disubstituted or higher-substituted hydroxyaromatics, for example the reaction of phenol and $H_2O_2$, or of phenol and mixtures which provide $H_2O_2$ in situ, to form hydroquinone;

oxime formation from ketones in the presence of $H_2O_2$, or mixtures which provide $H_2O_2$ in situ, and ammonia (ammonoximation), for example the preparation of cyclohexanone oxime from cyclohexanone;

the Baeyer-Villiger oxidation.

In the process of the present invention, organic compounds which have at least one C—C double bond are epoxidized.

Examples of such organic compounds having at least one C—C double bond are the following alkenes: ethene, propene, 1-butene, 2-butene, isobutene, butadiene, pentene, piperylene, hexenes, hexadienes, heptenes, octenes, diisobutene, trimethylpentene, nonenes, dodecene, tridecene, tetradecene to eicosene, tripropene and tetrapropene, polybutadienes, polyisobutenes, isoprenes, terpenes, geraniol, linalool, linalyl acetate, methylenecyclopropane, cyclopentene, cyclohexene, norbornene, cycloheptene, vinylcyclohexane, vinyloxiran, vinylcyclohexene, styrene, cyclooctene, cyclooctadiene, vinylnorbornene, indene, tetrahydroindene, methylstyrene, dicyclopentadiene, dinvinylbenzene, cyclododecene, cyclododecatriene, stilbene, diphenylbutadiene, vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

The process of the present invention is preferably carried out using alkenes having from 2 to 8 carbon atoms. Particular preference is given to reacting ethene, propylene and butene.

As has been mentioned above, metal-organic framework materials as such are described in, for example, U.S. Pat. No. 5,648,508, EP-A-0 709 253, M. O'Keeffe et al., *J Sol. State Chem.*, 152 (2000) p. 3–20, H. Li et al., *Nature* 402 (1999) p. 276 seq., M. Eddaoudi et al., *Topics in Catalysis* 9 (1999) p. 105–111, B. Chen et al., *Science* 291 (2001) p. 1021–23. An inexpensive way for the preparation of said materials is the subject of DE 10111230.0. The content of these publications, to which reference is made herein, is fully incorporated in the content of the present application.

The catalyst used in the present invention contains at least one of the metal-organic framework material, for example one of the materials described below.

The metal-organic framework materials, as used in the present invention, comprise pores, particularly micro- and/or mesopores. Micropores are defined as being pores having a diameter of 2 nm or below and mesopores as being pores having a diameter in the range of above 2 nm to 50 nm, respectively, according to the definition given in *Pure Applied Chem.* 45, p. 71 seq., particularly on p. 79 (1976). The presence of the micro- and/or mesopores can be monitored by sorption measurements for determining the capacity of the metal-organic framework materials to take up nitrogen at 77 K according to DIN 66131 and/or DIN 66134.

For example, a type-I-form of the isothermal curve indicates the presence of micropores [see, for example, paragraph 4 of M. Eddaoudi et al., *Topics in Catalysis* 9 (1999)]. In a preferred embodiment, the specific surface area, as calculated according to the Langmuir model (DIN 66131, 66134) preferably is above 5 m$^2$/g, further preferred above 10 m$^2$/g, more preferably above 50 m$^2$/g, particularly preferred above 500 m$^2$/g and may increase into the region of to above 3000 m$^2$/g.

As to the metal component within the framework material that is to be used according to the present invention, particularly to be mentioned are the metal ions of the main group elements and of the subgroup elements of the periodic system of the elements, namely of the groups Ia, Ia, IIIa, IVa to VIIIa and Ib to VIb. Among those metal components, particular reference is made to Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, and Bi, more preferably to Zn, Cu, Ni, Pd, Pt, Ru, Rh and Co. As to the metal ions of these elements, particular reference is made to: $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pt^{+}$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, $Bi^{5+}$, $Bi^{3+}$ and $Bi^{+}$.

With regard to the preferred metal ions and further details regarding the same, particular reference is made to: EP-A 0 790 253, particularly to p. 10, l. 8–30, section "The Metal Ions", which section is incorporated herein by reference.

In addition to the metal salts disclosed in EP-A 0 790 253 and U.S. Pat. No. 5,648,508, other metallic compounds can be used, such as sulfates, phosphates and other complex counter-ion metal salts of the main- and subgroup metals of the periodic system of the elements. Metal oxides, mixed oxides and mixtures of metal oxides and/or mixed oxides with or without a defined stoichiometry are preferred. All of the above mentioned metal compounds can be soluble or insoluble and they may be used as starting material either in form of a powder or as a shaped body or as any combination thereof.

As to the at least bidentate organic compound, which is capable to coordinate with the metal ion, in principle all compounds can be used which are suitable for this purpose and which fulfill the above requirements of being at least bidentate. Said organic compound must have at least two centers, which are capable to coordinate with the metal ions of a metal salt, particularly with the metals of the aforementioned groups. With regard to the at least bidentate organic compound, specific mention is to be made of compounds having i) an alkyl group substructure, having from 1 to 10 carbon atoms, ii) an aryl group substructure, having from 1 to 5 phenyl rings, iii) an alkyl or aryl amine substructure, consisting of alkyl groups having from 1 to 10 carbon atoms or aryl groups having from 1 to 5 phenyl rings, said substructures having bound thereto at least one at least bidentate functional group "X", which is covalently bound to the substructure of said compound, and wherein X is selected from the group consisting of $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_3$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings, and $CH(SH)_2$, $C(SH)_3$, $CH(NH_2)_2$, $C(NH_2)_2$, $CH(OH)_2$, $C(OH)_3$, $CH(CN)_2$ and $C(CN)_3$.

Particularly to be mentioned are substituted or unsubstituted, mono- or polynuclear aromatic di-, tri- and tetracarboxylic acids and substituted or unsubstituted, aromatic, at least one hetero atom comprising aromatic di-, tri- and tetracarboxylic acids, which have one or more nuclei.

A preferred ligand is 1,3,5-benzene tricarboxylate (BCT). Further preferred ligands are ADC (acetylene dicarboxylate), NDC (naphtalen dicarboxylate), BDC (benzene dicarboxylate), ATC (adamantane tetracarboxylate), BTC (benzene tri-carboxylate), BTB (benzene tribenzoate), MTB (methane tetrabenzoate) and ATB (adamantane tribenzoate).

Besides the at least bidentate organic compound, the framework material as used in accordance with the present invention may also comprise one or more mono-dentate ligand(s), which is/are preferably selected from the following mono-dentate substances and/or derivatives thereof:

a. alkyl amines and their corresponding alkyl ammonium salts, containing linear, branched, or cyclic aliphatic groups, having from 1 to 20 carbon atoms (and their corresponding ammonium salts);

b. aryl amines and their corresponding aryl ammonium salts having from 1 to 5 phenyl rings;

c. alkyl phosphonium salts, containing linear, branched, or cyclic aliphatic groups, having from 1 to 20 carbon atoms;

d. aryl phosphonium salts, having from 1 to 5 phenyl rings;

e. alkyl organic acids and the corresponding alkyl organic anions (and salts) containing linear, branched, or cyclic aliphatic groups, having from 1 to 20 carbon atoms;

f. aryl organic acids and their corresponding aryl organic anions and salts, having from 1 to 5 phenyl rings;

g. aliphatic alcohols, containing linear, branched, or cyclic aliphatic groups, having from 1 to 20 carbon atoms;

h. aryl alcohols having from 1 to 5 phenyl rings;

i. inorganic anions from the group consisting of: sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, bicarbonate, and the corresponding acids and salts of the aforementioned inorganic anions, j. ammonia, carbon dioxide, methane, oxygen, ethylene, hexane, benzene, toluene, xylene, chlorobenzene, nitrobenzene, naphthalene, thiophene, pyridine, acetone, 1-2-dichloroethane, methylenechloride, tetrahydrofuran, ethanolamine, triethylamine and trifluoromethylsulfonic acid.

Further details regarding the at least bidentate organic compounds and the mono-dentate substances, from which the ligands of the framework material as used in the present application are derived, can be taken from EP-A 0 790 253, whose respective content is incorporated into the present application by reference.

Within the present application, framework materials of the kind described herein, which comprise $Zn^{2+}$ as a metal ion and ligands derived from terephthalic acid as the bidentate compound, are particularly preferred. Said framework materials are known as MOF-5 in the literature.

Further metal ions and at least bidentate organic compounds and mono-dentate substances, which are respectively useful for the preparation of the framework materials used in the present invention as well as processes for their preparation are particularly disclosed in EP-A 0 790 253, U.S. Pat. No. 5,648,508 and DE 10111230.0.

As solvents, which are particularly useful for the preparation of MOF-5, in addition to the solvents disclosed in the above-referenced literature, dimethyl formamide, diethyl formamide and N-methylpyrollidone, alone, in combination with each other or in combination with other solvents may be used. Within the preparation of the framework materials, particularly within the preparation of MOF-5, the solvents and mother liquors are recycled after crystallization in order to save costs and materials.

The pore sizes of the metal-organic framework can be adjusted by selecting suitable organic ligands and/or bidendate compounds (=linkers). Generally, the larger the linker, the larger the pore size. Any pore size that is still supported by a the metal-organic framework in the absence of a host and at temperatures of at least 200° C. is conceivable. Pore sizes ranging from 0,2 nm to 30 nm are preferred, with pore sizes ranging from 0,3 nm to 3 nm being particularly preferred.

In the following, examples of metal-organic framework materials (MOFs) are given to illustrate the general concept given above. These specific examples, however, are not meant to limit the generality and scope of the present application.

By way of example, a list of metal-organic framework materials already synthesized and characterized is given below. This also includes novel isoreticular metal organic framework materials (IR-MOFs), which may be used in the context of the present application. Such materials having the same framework topology while displaying different pore sizes and crystal densities are described, for example in M. Eddouadi et al., *Science* 295 (2002) 469, whose respective content is incorporated into the present application by reference The solvents used are of particular importance for the synthesis of these materials and are therefore mentioned in the table. The values for the cell parameters (angles $\alpha$, $\beta$ and $\gamma$ as well as the spacings a, b and c, given in Angstrom) have been obtained by x-ray diffraction and represent the space group given in the table as well.

| MOF-n | Ingredients molar ratios M + L | Solvents | $\alpha$ | $\beta$ | $\gamma$ | a | b | c | Space Group |
|---|---|---|---|---|---|---|---|---|---|
| MOF-0 | $Zn(NO_3)_2 \cdot 6H_2O$ $H_3(BTC)$ | ethanol | 90 | 90 | 120 | 16.711 | 16.711 | 14.189 | P6(3)/Mcm |
| MOF-2 | $Zn(NO_3)_2 \cdot 6H_2O$ (0.246 mmol) $H_2(BDC)$ (0.241 mmol) | DMF toluene | 90 | 102.8 | 90 | 6.718 | 15.49 | 12.43 | P2(1)/n |
| MOF-3 | $Zn(NO_3)_2 \cdot 6H_2O$ (1.89 mmol) $H_2(BDC)$ (1.93 mmol) | DMF MeOH | 99.72 | 111.11 | 108.4 | 9.726 | 9.911 | 10.45 | P-1 |
| MOF-4 | $Zn(NO_3)_2 \cdot 6H_2O$ (1.00 mmol) $H_3(BTC)$ (0.5 mmol) | ethanol | 90 | 90 | 90 | 14.728 | 14.728 | 14.728 | P2(1)3 |
| MOF-5 | $Zn(NO_3)_2 \cdot 6H_2O$ (2.22 mmol) $H_2(BDC)$ (2.17 mmol) | DMF chlorobenzene | 90 | 90 | 90 | 25.669 | 25.669 | 25.669 | Fm-3m |
| MOF-38 | $Zn(NO_3)_2 \cdot 6H_2O$ (0.27 mmol) $H_3(BTC)$ (0.15 mmol) | DMF chlorobenzene | 90 | 90 | 90 | 20.657 | 20.657 | 17.84 | 14 cm |

-continued

| MOF-n | Ingredients molar ratios M + L | Solvents | α | β | γ | a | b | c | Space Group |
|---|---|---|---|---|---|---|---|---|---|
| MOF-31 Zn(ADC)$_2$ | Zn(NO$_3$)$_2$.6H$_2$O 0.4 mmol H$_2$(ADC) 0.8 mmol | ethanol | 90 | 90 | 90 | 10.821 | 10.821 | 10.821 | Pn(-3)m |
| MOF-12 Zn$_2$(ATC) | Zn(NO$_3$)$_2$.6H$_2$O 0.3 mmol H$_4$(ATC) 0.15 mmol | ethanol | 90 | 90 | 90 | 15.745 | 16.907 | 18.167 | Pbca |
| MOF-20 ZnNDC | Zn(NO$_3$)$_2$.6H$_2$O 0.37 mmol H$_2$NDC 0.36 mmol | DMF chloro- benzene | 90 | 92.13 | 90 | 8.13 | 16.444 | 12.807 | P2(1)/c |
| MOF-37 | Zn(NO$_3$)$_2$.6H$_2$O 0.2 mmol H$_2$NDC 0.2 mmol | DEF chloro- benzene | 72.38 | 83.16 | 84.33 | 9.952 | 11.576 | 15.556 | P-1 |
| MOF-8 Tb$_2$(ADC) | Tb(NO$_3$)$_3$.5H$_2$O 0.10 mmol H$_2$ADC 0.20 mmol | DMSO MeOH | 90 | 115.7 | 90 | 19.83 | 9.822 | 19.183 | C2/c |
| MOF-9 Tb$_2$(ADC) | Tb(NO$_3$)$_3$.5H$_2$O 0.08 mmol H$_2$ADB 0.12 mmol | DMSO | 90 | 102.09 | 90 | 27.056 | 16.795 | 28.139 | C2/c |
| MOF-6 | Tb(NO$_3$)$_3$.5H$_2$O 0.30 mmol H$_2$(BDC) 0.30 mmol | DMF MeOH | 90 | 91.28 | 90 | 17.599 | 19.996 | 10.545 | P21/c |
| MOF-7 | Tb(NO$_3$)$_3$.5H$_2$O 0.15 mmol H$_2$(BDC) 0.15 mmol | H$_2$O | 102.3 | 91.12 | 101.5 | 6.142 | 10.069 | 10.096 | P-1 |
| MOF-69A | Zn(NO$_3$)$_2$.6H$_2$O 0.083 mmol 4,4'BPDC 0.041 mmol | DEF H$_2$O$_2$ MeNH$_2$ | 90 | 111.6 | 90 | 23.12 | 20.92 | 12 | C2/c |
| MOF-69B | Zn(NO$_3$)$_2$.6H$_2$O 0.083 mmol 2,6-NCD 0.041 mmol | DEF H$_2$O$_2$ MeNH$_2$ | 90 | 95.3 | 90 | 20.17 | 18.55 | 12.16 | C2/c |
| MOF-11 Cu$_2$(ATC) | Cu(NO$_3$)$_2$.2.5H$_2$O 0.47 mmol H$_2$ATC 0.22 mmol | H$_2$O | 90 | 93.86 | 90 | 12.987 | 11.22 | 11.336 | C2/c |
| MOF-11 Cu$_2$(ATC) dehydr. | | | 90 | 90 | 90 | 8.4671 | 8.4671 | 14.44 | P42/mmc |
| MOF-14 Cu$_3$(BTB) | Cu(NO$_3$)$_2$.2.5H$_2$O 0.28 mmol H$_3$BTB 0.052 mmol | H$_2$O DMF EtOH | 90 | 90 | 90 | 26.946 | 26.946 | 26.946 | Im-3 |
| MOF-32 Cd(ATC) | Cd(NO$_3$)$_2$.4H$_2$O 0.24 mmol H$_4$ATC 0.10 mmol | H$_2$O NaOH | 90 | 90 | 90 | 13.468 | 13.468 | 13.468 | P(-4)3m |
| MOF-33 Zn$_2$(ATB) | ZnCl$_2$ 0.15 mmol H$_4$ATB 0.02 mmol | H$_2$O DMF EtOH | 90 | 90 | 90 | 19.561 | 15.255 | 23.404 | Imma |
| MOF-34 Ni(ATC) | Ni(NO$_3$)$_2$.6H$_2$O 0.24 mmol H$_4$ATC 0.10 mmol | H$_2$O NaOH | 90 | 90 | 90 | 10.066 | 11.163 | 19.201 | P2$_1$2$_1$2$_1$ |
| MOF-36 Zn$_2$(MTB) | Zn(NO$_3$)$_2$.4H$_2$O 0.20 mmol H$_4$MTB 0.04 mmol | H$_2$O DMF | 90 | 90 | 90 | 15.745 | 16.907 | 18.167 | Pbca |
| MOF-39 Zn$_3$O(HBTB) | Zn(NO$_3$)$_2$4H$_2$O 0.27 mmol H$_3$BTB 0.07 mmol | H$_2$O DMF EtOH | 90 | 90 | 90 | 17.158 | 21.591 | 25.308 | Pnma |
| NO305 | FeCl$_2$.4H$_2$O 5.03 mmol formic acid 86.90 mmol | DMF | 90 | 90 | 120 | 8.2692 | 8.2692 | 63.566 | R-3c |

-continued

| MOF-n | Ingredients molar ratios M + L | Solvents | α | β | γ | a | b | c | Space Group |
|---|---|---|---|---|---|---|---|---|---|
| NO306A | FeCl$_2$.4H$_2$O 5.03 mmol formic acid 86.90 mmol | DEF | 90 | 90 | 90 | 9.9364 | 18.374 | 18.374 | Pbcn |
| NO29 MOF-0 like | Mn(Ac)$_2$.4H$_2$O 0.46 mmol H$_3$BTC 0.69 mmol | DMF | 120 | 90 | 90 | 14.16 | 33.521 | 33.521 | P-1 |
| BPR48 A2 | Zn(NO$_3$)$_2$6H$_2$O 0.012 mmol H$_2$BDC 0.012 mmol | DMSO toluene | 90 | 90 | 90 | 14.5 | 17.04 | 18.02 | Pbca |
| BPR69 B1 | Cd(NO$_3$)$_2$4H$_2$O 0.0212 mmol H$_2$BDC 0.0428 mmol | DMSO | 90 | 98.76 | 90 | 14.16 | 15.72 | 17.66 | Cc |
| BPR92 A2 | Co(NO$_3$)$_2$.6H$_2$O 0.018 mmol H$_2$BDC 0.018 mmol | NMP | 106.3 | 107.63 | 107.2 | 7.5308 | 10.942 | 11.025 | P1 |
| BPR95 C5 | Cd(NO$_3$)$_2$4H$_2$O 0.012 mmol H$_2$BDC 0.36 mmol | NMP | 90 | 112.8 | 90 | 14.460 | 11.085 | 15.529 | P2(1)/n |
| CuC$_6$H$_4$O$_6$ | Cu(NO$_3$)$_2$.2.5H$_2$O 0.370 mmol H$_2$BDC(OH)$_2$ 0.37 mmol | DMF chloro-benzene | 90 | 105.29 | 90 | 15.259 | 14.816 | 14.13 | P2(1)/c |
| M(BTC) MOF-0 like | Co(SO$_4$)H$_2$O 0.055 mmol H$_3$BTC 0.037 mmol | DMF | | Same as MOF-0 | | | | | |
| Tb(C$_6$H$_4$O$_6$) | Tb(NO$_3$)$_3$.5H$_2$O 0.370 mmol H$_2$(C$_6$H$_4$O$_6$) 0.56 mmol | DMF chloro-benzene | 104.6 | 107.9 | 97.147 | 10.491 | 10.981 | 12.541 | P-1 |
| Zn(C$_2$O$_4$) | ZnCl$_2$ 0.370 mmol oxalic acid 0.37 mmol | DMF chloro-benzene | 9.0 | 120 | 90 | 9.4168 | 9.4168 | 8.464 | P(-3)/m |
| Co(CHO) | Co(NO$_3$)$_2$.5H$_2$O 0.043 mmol formic acid 1.60 mmol | DMF | 90 | 91.32 | 90 | 11.328 | 10.049 | 14.854 | P2(1)/n |
| Cd(CHO) | Cd(NO$_3$)$_2$.4H$_2$O 0.185 mmol formic acid 0.15 mmol | DMF | 90 | 120 | 90 | 8.5168 | 8.5168 | 22.674 | R-3c |
| Cu(C$_3$H$_2$O$_4$) | Cu(NO$_3$)$_2$.2.5H$_2$O 0.043 mmol malonic acid 0.192 mmol | DMF | 90 | 90 | 90 | 8.366 | 8.366 | 11.919 | P43 |
| Zn$_6$(NDC)$_5$ MOF-48 | Zn(NO$_3$)$_2$.6H$_2$O 0.097 mmol 14 NDC 0.069 mmol | DMF chloro-benzene H$_2$O$_2$ | 90 | 95.902 | 90 | 19.504 | 16.482 | 14.64 | C2/m |
| MOF-47 | Zn(NO$_3$)$_2$6H$_2$O 0.185 mmol H$_2$(BDC[CH$_3$]$_4$) 0.185 mmol | DMF chloro-benzene H$_2$O$_2$ | 90 | 92.55 | 90 | 11.303 | 16.029 | 17.535 | P2(1)/c |
| MO25 | Cu(NO$_3$)$_2$.2.5H$_2$O 0.084 mmol BPhDC 0.085 mmol | DMF | 90 | 112.0 | 90 | 23.880 | 16.834 | 18.389 | P2(1)/c |
| Cu-Thio | Cu(NO$_3$)$_2$.2.5H$_2$O 0.084 mmol thiophene dicarboxylic 0.085 mmol | DEF | 90 | 113.6 | 90 | 15.4747 | 14.514 | 14.032 | P2(1)/c |
| ClBDC1 | Cu(NO$_3$)$_2$.2.5H$_2$O 0.084 mmol H$_2$(BDCCl$_2$) 0.085 mmol | DMF | 90 | 105.6 | 90 | 14.911 | 15.622 | 18.413 | C2/c |

-continued

| MOF-n | Ingredients molar ratios M + L | Solvents | α | β | γ | a | b | c | Space Group |
|---|---|---|---|---|---|---|---|---|---|
| MOF-101 | Cu(NO$_3$)$_2$.2.5H$_2$O 0.084 mmol BrBDC 0.085 mmol | DMF | 90 | 90 | 90 | 21.607 | 20.607 | 20.073 | Fm3m |
| Zn$_3$(BTC)$_2$ | ZnCl$_2$ 0.033 mmol H$_3$BTC 0.033 mmol | DMF EtOH base added | 90 | 90 | 90 | 26.572 | 26.572 | 26.572 | Fm-3m |
| MOF-j | Co(CH$_3$CO$_2$)$_2$.4H$_2$O (1.65 mmol) H$_3$(BZC) (0.95 mmol) | H$_2$O | 90 | 112.0 | 90 | 17.482 | 12.963 | 6.559 | C2 |
| MOF-n | Zn(NO$_3$)$_2$.6H$_2$O H$_3$(BTC) | ethanol | 90 | 90 | 120 | 16.711 | 16.711 | 14.189 | P6(3)/mcm |
| PbBDC | Pb(NO$_3$)$_2$ (0.181 mmol) H$_2$(BDC) (0.181 mmol) | DMF ethanol | 90 | 102.7 | 90 | 8.3639 | 17.991 | 9.9617 | P2(1)/n |
| Znhex | Zn(NO$_3$)$_2$.6H$_2$O (0.171 mmol) H$_3$BTB (0.114 mmol) | DMF p-xylene ethanol | 90 | 90 | 120 | 37.1165 | 37.117 | 30.019 | P3(1)c |
| AS16 | FeBr$_2$ 0.927 mmol H$_2$(BDC) 0.927 mmol | DMF anhydr. | 90 | 90.13 | 90 | 7.2595 | 8.7894 | 19.484 | P2(1)c |
| AS27-2 | FeBr$_2$ 0.927 mmol H$_3$(BDC) 0.464 mmol | DMF anhydr. | 90 | 90 | 90 | 26.735 | 26.735 | 26.735 | Fm3m |
| AS32 | FeCl$_3$ 1.23 mmol H$_2$(BDC) 1.23 mmol | DMF anhydr. ethanol | 90 | 90 | 120 | 12.535 | 12.535 | 18.479 | P6(2)c |
| AS54-3 | FeBr$_2$ 0.927 BPDC 0.927 mmol | DMF anhydr. n-propanol | 90 | 109.98 | 90 | 12.019 | 15.286 | 14.399 | C2 |
| AS61-4 | FeBr$_2$ 0.927 mmol m-BDC 0.927 mmol | pyridine anhydr. | 90 | 90 | 120 | 13.017 | 13.017 | 14.896 | P6(2)c |
| AS68-7 | FeBr$_2$ 0.927 mmol m-BDC 1.204 mmol | DMF anhydr. Pyridine | 90 | 90 | 90 | 18.3407 | 10.036 | 18.039 | Pca2$_1$ |
| Zn(ADC) | Zn(NO$_3$)$_2$.6H$_2$O 0.37 mmol H$_2$(ADC) 0.36 mmol | DMF chloro-benzene | 90 | 99.85 | 90 | 16.764 | 9.349 | 9.635 | C2/c |
| MOF-12 Zn$_2$(ATC) | Zn(NO$_3$)$_2$.6H$_2$O 0.30 mmol H$_4$(ATC) 0.15 mmol | ethanol | 90 | 90 | 90 | 15.745 | 16.907 | 18.167 | Pbca |
| MOF-20 ZnNDC | Zn(NO$_3$)$_2$.6H$_2$O 0.37 mmol H$_2$NDC 0.36 mmol | DMF chloro-benzene | 90 | 92.13 | 90 | 8.13 | 16.444 | 12.807 | P2(1)/c |
| MOF-37 | Zn(NO$_3$)$_2$.6H$_2$O 0.20 mmol H$_2$NDC 0.20 mmol | DEF chloro-benzene | 72.38 | 83.16 | 84.33 | 9.952 | 11.576 | 15.556 | P-1 |
| Zn(NDC) (DMSO) | Zn(NO$_3$)$_2$.6H$_2$O H$_2$NDC | DMSO | 68.08 | 75.33 | 88.31 | 8.631 | 10.207 | 13.114 | P-1 |
| Zn(NDC) | Zn(NO$_3$)$_2$.6H$_2$O H$_2$NDC | | 90 | 99.2 | 90 | 19.289 | 17.628 | 15.052 | C2/c |
| Zn(HPDC) | Zn(NO$_3$)$_2$.4H$_2$O 0.23 mmol H$_2$(HPDC) 0.05 mmol | DMF H$_2$O | 107.9 | 105.06 | 94.4 | 8.326 | 12.085 | 13.767 | P-1 |
| Co(HPDC) | Co(NO$_3$)$_2$.6H$_2$O 0.21 mmol H$_2$(HPDC) 0.06 mmol | DMF H$_2$O/ ethanol | 90 | 97.69 | 90 | 29.677 | 9.63 | 7.981 | C2/c |

-continued

| MOF-n | Ingredients molar ratios M + L | Solvents | α | β | γ | a | b | c | Space Group |
|---|---|---|---|---|---|---|---|---|---|
| Zn₃(PDC)2.5 | Zn(NO₃)₂.4H₂O 0.17 mmol H₂(HPDC) 0.05 mmol | DMF/ ClBz H₂O/ TEA | 79.34 | 80.8 | 85.83 | 8.564 | 14.046 | 26.428 | P-1 |
| Cd₂(TPDC)2 | Cd(NO₃)₂.4H₂O 0.06 mmol H₂(HPDC) 0.06 mmol | methanol/ CHP H₂O | 70.59 | 72.75 | 87.14 | 10.102 | 14.412 | 14.964 | P-1 |
| Tb(PDC)1.5 | Tb(NO₃)₃.5H₂O 0.21 mmol H₂(PDC) 0.034 mmol | DMF H₂O/ ethanol | 109.8 | 103.61 | 100.14 | 9.829 | 12.11 | 14.628 | P-1 |
| ZnDBP | Zn(NO₃)₂.6H₂O 0.05 mmol dibenzylphosphate 0.10 mmol | MeOH | 90 | 93.67 | 90 | 9.254 | 10.762 | 27.93 | P2/n |
| Zn₃(BPDC) | ZnBr₂ 0.021 mmol 4,4'BPDC 0.005 mmol | DMF | 90 | 102.76 | 90 | 11.49 | 14.79 | 19.18 | P21/n |
| CdBDC | Cd(NO₃)₂.4H₂O 0.100 mmol H₂(BDC) 0.401 mmol | DMF Na₂SiO₃ (aq) | 90 | 95.85 | 90 | 11.2 | 11.11 | 16.71 | P21/n |
| Cd-mBDC | Cd(NO₃)₂.4H₂O 0.009 mmol H₂(mBDC) 0.018 mmol | DMF MeNH₂ | 90 | 101.1 | 90 | 13.69 | 18.25 | 14.91 | C2/c |
| Zn₄OBNDC | Zn(NO₃)₂.6H₂O 0.041 mmol BNDC | DEF MeNH₂ H₂O₂ | 90 | 90 | 90 | 22.35 | 26.05 | 59.56 | Fmmm |
| Eu(TCA) | Eu(NO₃)₃.6H₂O 0.14 mmol TCA 0.026 mmol | DMF chloro- benzene | 90 | 90 | 90 | 23.325 | 23.325 | 23.325 | Pm-3n |
| Tb(TCA) | Tb(NO₃)₃.6H₂O 0.069 mmol TCA 0.026 mmol | DMF chloro- benzene | 90 | 90 | 90 | 23.272 | 23.272 | 23.372 | Pm-3n |
| Formate | Ce(NO₃)₃.6H₂O 0.138 mmol Formic acid 0.43 mmol | H₂O ethanol | 90 | 90 | 120 | 10.668 | 10.667 | 4.107 | R-3m |
|  | FeCl₂.4H₂O 5.03 mmol Formic acid 86.90 mmol | DMF | 90 | 90 | 120 | 8.2692 | 8.2692 | 63.566 | R-3c |
|  | FeCl₂.4H₂O 5.03 mmol Formic acid 86.90 mmol | DEF | 90 | 90 | 90 | 9.9364 | 18.374 | 18.374 | Pbcn |
|  | FeCl₂.4H₂O 5.03 mmol Formic acid 86.90 mmol | DEF | 90 | 90 | 90 | 8.335 | 8.335 | 13.34 | P-31c |
| NO330 | FeCl₂.4H₂O 0.50 mmol Formic acid 8.69 mmol | form- amide | 90 | 90 | 90 | 8.7749 | 11.655 | 8.3297 | Pnna |
| NO332 | FeCl₂.4H₂O 0.50 mmol Formic acid 8.69 mmol | DIP | 90 | 90 | 90 | 10.0313 | 18.808 | 18.355 | Pbcn |
| NO333 | FeCl₂.4H₂O 0.50 mmol Formic acid 8.69 mmol | DBF | 90 | 90 | 90 | 45.2754 | 23.861 | 12.441 | Cmcm |
| NO335 | FeCl₂.4H₂O 0.50 mmol Formic acid 8.69 mmol | CHF | 90 | 91.372 | 90 | 11.5964 | 10.187 | 14.945 | P21/n |
| NO336 | FeCl₂.4H₂O 0.50 mmol Formic acid 8.69 mmol | MFA | 90 | 90 | 90 | 11.7945 | 48.843 | 8.4136 | Pbcm |

-continued

| MOF-n | Ingredients molar ratios M + L | Solvents | α | β | γ | a | b | c | Space Group |
|---|---|---|---|---|---|---|---|---|---|
| NO13 | Mn(Ac)$_2$.4H$_2$O 0.46 mmol Bezoic acid 0.92 mmol Bipyridine 0.46 mmol | ethanol | 90 | 90 | 90 | 18.66 | 11.762 | 9.418 | Pbcn |
| NO29 MOF-0 like | Mn(Ac)$_2$.4H$_2$O 0.46 mmol H$_3$BTC 0.69 mmol | DMF | 120 | 90 | 90 | 14.16 | 33.521 | 33.521 | P-1 |
| Mn(hifac)$_2$ (O$_2$CC$_6$H$_5$) | Mn(Ac)$_2$.4H$_2$O 0.46 mmol Hfac 0.92 mmol Bipyridine 0.46 mmol | ether | 90 | 95.32 | 90 | 9.572 | 17.162 | 14.041 | C2/c |
| BPR43G2 | Zn(NO$_3$)$_2$.6H$_2$O 0.0288 mmol H$_2$BDC 0.0072 mmol | DMF CH$_3$CN | 90 | 91.37 | 90 | 17.96 | 6.38 | 7.19 | C2/c |
| BPR48A2 | Zn(NO$_3$)$_2$6H$_2$O 0.012 mmol H$_2$BDC 0.012 mmol | DMSO toluene | 90 | 90 | 90 | 14.5 | 17.04 | 18.02 | Pbca |
| BPR49B1 | Zn(NO$_3$)$_2$6H$_2$O 0.024 mmol H$_2$BDC 0.048 mmol | DMSO methanol | 90 | 91.172 | 90 | 33.181 | 9.824 | 17.884 | C2/c |
| BPR56E1 | Zn(NO$_3$)$_2$6H$_2$O 0.012 mmol H$_2$BDC 0.024 mmol | DMSO n-propanol | 90 | 90.096 | 90 | 14.5873 | 14.153 | 17.183 | P2(1)/n |
| BPR68D10 | Zn(NO$_3$)$_2$6H$_2$O 0.0016 mmol H$_3$BTC 0.0064 mmol | DMSO benzene | 90 | 95.316 | 90 | 10.0627 | 10.17 | 16.413 | P2(1)/c |
| BPR69B1 | Cd(NO$_3$)$_2$4H$_2$O 0.0212 mmol H$_2$BDC 0.0428 mmol | DMSO | 90 | 98.76 | 90 | 14.16 | 15.72 | 17.66 | Cc |
| BPR73E4 | Cd(NO$_3$)$_2$4H$_2$O 0.006 mmol H$_2$BDC 0.003 mmol | DMSO toluene | 90 | 92.324 | 90 | 8.7231 | 7.0568 | 18.438 | P2(1)/n |
| BPR76D5 | Zn(NO$_3$)$_2$6H$_2$O 0.0009 mmol H$_2$BzPDC 0.0036 mmol | DMSO | 90 | 104.17 | 90 | 14.4191 | 6.2599 | 7.0611 | Pc |
| BPR80B5 | Cd(NO$_3$)$_2$.4H$_2$O 0.018 mmol H$_2$BDC 0.036 mmol | DMF | 90 | 115.11 | 90 | 28.049 | 9.184 | 17.837 | C2/c |
| BPR80H5 | Cd(NO$_3$)$_2$4H$_2$O 0.027 mmol H$_2$BDC 0.027 mmol | DMF | 90 | 119.06 | 90 | 11.4746 | 6.2151 | 17.268 | P2/c |
| BPR82C6 | Cd(NO$_3$)$_2$4H$_2$O 0.0068 mmol H$_2$BDC 0.202 mmol | DMF | 90 | 90 | 90 | 9.7721 | 21.142 | 27.77 | Fdd2 |
| BPR86C3 | Cd(NO$_3$)$_2$6H$_2$O 0.0025 mmol H$_2$BDC 0.075 mmol | DMF | 90 | 90 | 90 | 18.3449 | 10.031 | 17.983 | Pca2(1) |
| BPR86H6 | Cd(NO$_3$)$_2$.6H$_2$O 0.010 mmol H$_2$BDC 0.010 mmol | DMF | 80.98 | 89.69 | 83.412 | 9.8752 | 10.263 | 15.362 | P-1 |
|  | Co(NO$_3$)$_2$6H$_2$O | NMP | 106.3 | 107.63 | 107.2 | 7.5308 | 10.942 | 11.025 | P1 |
| BPR95A2 | Zn(NO$_3$)$_2$6H$_2$O 0.012 mmol H$_2$BDC 0.012 mmol | NMP | 90 | 102.9 | 90 | 7.4502 | 13.767 | 12.713 | P2(1)/c |

-continued

| MOF-n | Ingredients molar ratios M + L | Solvents | α | β | γ | a | b | c | Space Group |
|---|---|---|---|---|---|---|---|---|---|
| $CuC_6F_4O_4$ | $Cu(NO_3)_2 \cdot 2.5H_2O$ 0.370 mmol $H_2BDC(OH)_2$ 0.37 mmol | DMF chloro-benzene | 90 | 98.834 | 90 | 10.9675 | 24.43 | 22.553 | P2(1)/n |
| Fe Formic | $FeCl_2 \cdot 4H_2O$ 0.370 mmol Formic acid 0.37 mmol | DMF | 90 | 91.543 | 90 | 11.495 | 9.963 | 14.48 | P2(1)/n |
| Mg Formic | $Mg(NO_3)_2 \cdot 6H_2O$ 0.370 mmol Formic acid 0.37 mmol | DMF | 90 | 91.359 | 90 | 11.383 | 9.932 | 14.656 | P2(1)/n |
| $MgC_6H_4O_6$ | $Mg(NO_3)_2 \cdot 6H_2O$ 0.370 mmol $H_2BDC(OH)_2$ 0.37 mmol | DMF | 90 | 96.624 | 90 | 17.245 | 9.943 | 9.273 | C2/c |
| $ZnC_2H_4BDC$ MOF-38 | $ZnCl_2$ 0.44 mmol CBBDC 0.261 mmol | DMF | 90 | 94.714 | 90 | 7.3386 | 16.834 | 12.52 | P2(1)/n |
| MOF-49 | $ZnCl_2$ 0.44 mmol m-BDC 0.261 mmol | DMF CH3CN | 90 | 93.459 | 90 | 13.509 | 11.984 | 27.039 | P2/c |
| MOF-26 | $Cu(NO_3)_2 \cdot 5H_2O$ 0.084 mmol DCPE 0.085 mmol | DMF | 90 | 95.607 | 90 | 20.8797 | 16.017 | 26.176 | P2(i)/n |
| MOF-112 | $Cu(NO_3)_2 \cdot 2.5H_2O$ 0.084 mmol o-Br-m-BDC 0.085 mmol | DMF ethanol | 90 | 107.49 | 90 | 29.3241 | 21.297 | 18.069 | C2/c |
| MOF-109 | $Cu(NO_3)_2 \cdot 2.5H_2O$ 0.084 mmol KDB 0.085 mmol | DMF | 90 | 111.98 | 90 | 23.8801 | 16.834 | 18.389 | P2(1)/c |
| MOF-111 | $Cu(NO_3)_2 \cdot 2.5H_2O$ 0.084 mmol o-BrBDC 0.085 mmol | DMF ethanol | 90 | 102.16 | 90 | 10.6767 | 18.781 | 21.052 | C2/c |
| MOF-110 | $Cu(NO_3)_2 \cdot 2.5H_2O$ 0.084 mmol thiophene dicarboxylic 0.085 mmol | DMF | 90 | 90 | 120 | 20.0652 | 20.065 | 20.747 | R-3/m |
| MOF-107 | $Cu(NO_3)_2 \cdot 2.5H_2O$ 0.084 mmol thiophene dicarboxylic 0.085 mmol | DEF | 104.8 | 97.075 | 95.206 | 11.032 | 18.067 | 18.452 | P-1 |
| MOF-108 | $Cu(NO_3)_2 \cdot 2.5H_2O$ 0.084 mmol thiophene dicarboxylic 0.085 mmol | DBF/ methanol | 90 | 113.63 | 90 | 15.4747 | 14.514 | 14.032 | C2/c |
| MOF-102 | $Cu(NO_3)_2 \cdot 2.5H_2O$ 0.084 mmol $H_2(BDCCl_2)$ 0.085 mmol | DMF | 91.63 | 106.24 | 112.01 | 9.3845 | 10.794 | 10.831 | P-1 |
| Clbdc1 | $Cu(NO_3)_2 \cdot 2.5H_2O$ 0.084 mmol $H_2(BDCCl_2)$ 0.085 mmol | DEF | 90 | 105.56 | 90 | 14.911 | 15.622 | 18.413 | P-1 |
| Cu(NMOP) | $Cu(NO_3)_2 \cdot 2.5H_2O$ 0.084 mmol NBDC 0.085 mmol | DMF | 90 | 102.37 | 90 | 14.9238 | 18.727 | 15.529 | P2(1)/m |
| Tb(BTC) | $Tb(NO_3)_3 \cdot 5H_2O$ 0.033 mmol $H_3BTC$ 0.033 mmol | DMF | 90 | 106.02 | 90 | 18.6986 | 11.368 | 19.721 | |
| $Zn_3(BTC)_2$ Honk | $ZnCl_2$ 0.033 mmol $H_3BTC$ 0.033 mmol | DMF ethanol | 90 | 90 | 90 | 26.572 | 26.572 | 26.572 | Fm-3m |

-continued

| MOF-n | Ingredients molar ratios M + L | Solvents | α | β | γ | a | b | c | Space Group |
|---|---|---|---|---|---|---|---|---|---|
| Zn₄O(NDC) | Zn(NO₃)₂.4H₂O 0.066 mmol 14NDC 0.066 mmol | DMF ethanol | 90 | 90 | 90 | 41.5594 | 18.818 | 17.574 | aba |
| CdTDC | Cd(NO₃)₂.4H₂O 0.014 mmol thiophene 0.040 mmol DABCO 0.020 mmol | DMF H₂O | 90 | 90 | 90 | 12.173 | 10.485 | 7.33 | Pmma |
| IRMOF-2 | Zn(NO₃)₂.4H₂O 0.160 mmol o-Br-BDC 0.60 mmol | DEF | 90 | 90 | 90 | 25.772 | 25.772 | 25.772 | Fm-3m |
| IRMOF-3 | Zn(NO₃)₂.4H₂O 0.20 mmol H₂N—BDC 0.60 mmol | DEF ethanol | 90 | 90 | 90 | 25.747 | 25.747 | 25.747 | Fm-3m |
| IRMOF-4 | Zn(NO₃)₂.4H₂O 0.11 mmol [C₃H₇O]₂—BDC 0.48 mmol | DEF | 90 | 90 | 90 | 25.849 | 25.849 | 25.849 | Fm-3m |
| IRMOF-5 | Zn(NO₃)₂.4H₂O 0.13 mmol [C₅H₁₁O]₂—BDC 0.50 mmol | DEF | 90 | 90 | 90 | 12.882 | 12.882 | 12.882 | Pm-3m |
| IRMOF-6 | Zn(NO₃)₂.4H₂O 0.20 mmol [C₂H₄]—BDC 0.60 mmol | DEF | 90 | 90 | 90 | 25.842 | 25.842 | 25.842 | Fm-3m |
| IRMOF-7 | Zn(NO₃)₂.4H₂O 0.07 mmol 1,4NDC 0.20 mmol | DEF | 90 | 90 | 90 | 12.914 | 12.914 | 12.914 | Pm-3m |
| IRMOF-8 | Zn(NO₃)₂.4H₂O 0.55 mmol 2,6NDC 0.42 mmol | DEF | 90 | 90 | 90 | 30.092 | 30.092 | 30.092 | Fm-3m |
| IRMOF-9 | Zn(NO₃)₂.4H₂O 0.05 mmol BPDC 0.42 mmol | DEF | 90 | 90 | 90 | 17.147 | 23.322 | 25.255 | Pnnm |
| IRMOF-10 | Zn(NO₃)₂.4H₂O 0.02 mmol BPDC 0.012 mmol | DEF | 90 | 90 | 90 | 34.281 | 34.281 | 34.281 | Fm-3m |
| IRMOF-11 | Zn(NO₃)₂.4H₂O 0.05 mmol HPDC 0.20 mmol | DEF | 90 | 90 | 90 | 24.822 | 24.822 | 56.734 | R-3m |
| IRMOF-12 | Zn(NO₃)₂.4H₂O 0.017 mmol HPDC 0.12 mmol | DEF | 90 | 90 | 90 | 34.281 | 34.281 | 34.281 | Fm-3m |
| IRMOF-13 | Zn(NO₃)₂.4H₂O 0.048 mmol PDC 0.31 mmol | DEF | 90 | 90 | 90 | 24.822 | 24.822 | 56.734 | R-3m |
| IRMOF-14 | Zn(NO₃)₂.4H₂O 0.17 mmol PDC 0.12 mmol | DEF | 90 | 90 | 90 | 34.381 | 34.381 | 34.381 | Fm-3m |
| IRMOF-15 | Zn(NO₃)₂.4H₂O 0.063 mmol TPDC 0.025 mmol | DEF | 90 | 90 | 90 | 21.459 | 21.459 | 21.459 | Im-3m |
| IRMOF-16 | Zn(NO₃)₂.4H₂O 0.0126 mmol TPDC 0.05 mmol | DEF NMP | 90 | 90 | 90 | 21.49 | 21.49 | 21.49 | Pm-3m |

| | |
|---|---|
| ADC | Acetylene dicarboxylic acid |
| NDC | Naphtalene dicarboxylic acid |
| BDC | Benzene dicarboxylic acid |
| ATC | Adamantane tetracarboxylic acid |
| BTC | Benzene tricarboxylic acid |
| BTB | Benzene tribenzoate |
| MTB | Methane tetrabenzoate |
| ATB | Adamantane tetrabenzoate |
| ADB | Adamantane dibenzoate |

Examples for the synthesis of these materials as such can, for example, be found in: J. Am. Chem. Soc. 123 (2001) pages 8241ff or in Acc. Chem. Res. 31 (1998) pages 474ff, which are fully encompassed within the content of the present application with respect to their respective content.

The separation of the framework materials, particularly of MOF-5, from the mother liquor of the crystallization may be achieved by procedures known in the art such as solid-liquid separations, centrifugation, extraction, filtration, membrane filtration, cross-flow filtration, flocculation using flocculation adjuvants (non-ionic, cationic and anionic adjuvants) or by the addition of pH shifting additives such as salts, acids or bases, by flotation, as well as by evaporation of the mother liquor at elevated temperature and/or in vacuo and concentrating of the solid. The material obtained in this step is typically a fine powder and cannot be used for most practical applications, e.g. in catalysis, where shaped bodies are required.

The invention is now further described by way of the following examples, which are, however, not meant to limit the scope of the present application.

EXAMPLE 1

Preparation of a Catalyst According to the Invention

The following materials were used to prepare one catalyst according to the invention, containing MOF-5 as the porous material and Ag as an active metal:

| Starting Material | Molar Amount | Calculated | Experimental |
|---|---|---|---|
| AgNO$_3$ | 25.9 mmol | 4.3 g | 4.4 g |
| DEF | 904.6 mmol | 91.5 g | 91.5 g |
| MOF-5 | | 4.2 g | 4.2 g |
| acetontrile | | 33.0 g | 33.0 g |

The AgNO$_3$ (Merck) is dissolved in DEF (diethylformamide) and acetonitrile in a beaker. This clear solution is then added to an autoclave (250 ml volume) which already contains the MOF-5.

The crystallization occurred at 60° C. and within twenty hours. Subsequently, the solution was cooled and the solvent was decanted from the black crystals. Said crystals were washed in chloroforme until the chloroforme almost showed no color anymore. The catalyst was dried in vacuo until no more change in weigth occured. The yield is 4.7 g with a silver content of 15.3% by weight.

Example 2

Using the Catalyst from Example 1 for the catalysis of epoxidation reactions

In a gas phase flow apparatus (tubular reactor with 9 mm inner diameter, 150 mm reactor length), 500 mg of the catalyst prepared according to Example 1 are filled as a micro fixed bed. A mixture of oxygen, helium and propylene in the volume ratio of 66:24:10 is streamed over the catalyst at a temperature of 220° C. The effluent stream is analyzed by means of gas chromatography.

After a running time of 10 hours, the turnover with respect to propylene is 4.3% with the selectivity with respect to propylene oxide being 8.2%. After 15 hours, a turnover of 3.3% at a selectivity of 10.3% is obtained.

What is claimed is:

1. A process for the epoxidation of organic compounds, comprising reacting at least one organic compound with at least one epoxidizing agent in the presence of a catalyst, wherein the catalyst comprises a porous metal-organic framework material comprising at least one metal ion and at least one at least bidentate organic compound which is coordinately bound to said metal ion.

2. The process according to claim 1, wherein said epoxidizing agent is selected from the group consisting of a hydroperoxide, O$_2$, ozone, nitric oxides, and reactive oxides.

3. The process according to claim 2, wherein the hydroperoxide is selected from the group consisting of hydrogen peroxide, ethylbenzene peroxide, and cumenehydroperoxide.

4. The process according to claim 1, wherein said organic compound has at least one C—C double bond.

5. The process according to claim 4, wherein said organic compound with at least one C—C double bond is an alkene having 2 to 8 carbon atoms.

6. The process according to claim 1, wherein the metal ion is selected from the group consisting of $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^+$, $Ir^{2+}$, $Ir^+$, $Ni^{2+}$, $Ni^+$, $Pd^{2+}$, $Pd^+$, $Pt^{2+}$, $Pt^+$, $Cu^{2+}$, $Cu^+$, $Ag^+$, $Au^+$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^+$, $Sb^{5+}$, $Sb^{3+}$, $Sb^+$, $Bi^{5+}$, $Bi^{3+}$, $Bi^+$.

7. The process according to claim 5, wherein said alkene is selected from the group consisting of ethene, propene, 1-butene, 2-butene, isobutene, butadiene, pentene, and hexenes.

8. The process according to claim 1, wherein said organic compound is selected from the group consisting of ethene, propene, 1-butene, 2-butene, isobutene, butadiene, pentene, piperylene, hexenes, hexadienes, heptenes, octenes, diisobutene, trimethylpentene, nonenes, dodecene, tridecene, tetradecene, eicosene, tripropene, tetrapropene, polybutadienes, polyisobutenes, isoprenes, terpenes, geraniol, linalool, linalyl acetate, methylenecyclopropane, cyclopentene, cyclohexene, norbornene, cycloheptene, vinylcyclohexane, vinyloxiran, vinylcyclohexene, styrene, cyclooctene, cyclooctadiene, vinylnorbornene, indene, tetrahydroindene, methylstyrene, dicyclopentadiene, dinvinylbenzene, cyclododecene, cyclododecatriene, stilbene, diphenylbutadiene, vitamin A, beta-carotene, vinylidene fluoride, allylhalides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenol, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

9. The process according to claim 1, wherein the metal-organic framework material is microporous.

10. The process according to claim 1, wherein the metal-organic framework material is mesoporous.

11. The process according to claim 1, wherein the bidentate organic compound has a functional group selected from the group consisting of $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_3$, $PO_3H$, $AsO_3H$, $AsO_4H$, $P(SH)_3$, $As(SH)_3$, $CH(RSH)_2$, $C(RSH)_3$, $CH(RNH)_2$, $C(RNH_2)_3$, $CH(ROH)_2$, $C(ROH)_3$, $CH(RCN)_2$, $C(RCN)_3$, wherein R is an alkyl group having from 1 to 5 carbon atoms, or an aryl group consisting of 1 to 2 phenyl rings, and $CH(SH)_2$, $C(SH)_3$, $CH(NH_2)_2$, $C(NH_2)_2$, $CH(OH)_2$, $C(OH)_3$, $CH(CN)_2$ and $C(CN)_3$.

12. The process according to claim 1, wherein the bidentate organic compound is selected from the group consisting of 1,3,5-benzene tricarboxylate, acetylene dicarboxylate, naphtalen dicarboxylate, benzene dicarboxylate, adamantane tetracarboxylate, benzene tricarboxylate, benzene tribenzoate, methane tetrabenzoate, and adamantane tribenzoate.

13. The process according to claim 1, wherein the metal-organic framework material further comprises at least one monodentate ligand.

14. The process according to claim 1, wherein the monodentate ligand is selected from the group consisting of alkyl amines and ammonium salts therof; aryl amines and ammonium salts therof; alkyl phosphonium salts; aryl phosphonium salts; alkyl organic acids and salts thereof; aryl organic acids and salts thereof; aliphatic alcohols; aryl alcohols; inorganic sufates, nitrates, nitrites, sulfites, phosphates, hydrogen phosphates, dihydrogen phosphates, diphosphates, triphosphates, phosphites, chlorides, chlorates, bromides, bromates, iodides, iodates, carbonates, bicarbonates, and salts or acids thereof; ammonia, carbon dioxide, methane, oxygen, ethylene, hexane, benzene, toluene, xylene, chlorobenzene, nitrobenzene, naphthalene, thiophene, pyridine, acetone, 1,2-dichloroethane, methylene chloride, tetrahydrofuran, ethanolamine, thriethylamine, and trifluoromethylsulfonic acid.

15. The process according to claim 1, wherein the metal ion is $Zn^+$ and the bidentate organic compound is terphthalic acid.

16. The process according to claim 1, wherein the pores of the metal-organic framework have a size in the range of from 0.2 to 30 nm.

17. The process according to claim 16, wherein the pores of the metal-organic framework have a size in the range of from 0.3 to 3 nm.

18. The process according to claim 1, wherein the catalyst further comprises an active metal.

* * * * *